United States Patent [19]

Timmons et al.

[11] Patent Number: 5,188,885

[45] Date of Patent: Feb. 23, 1993

[54] NONWOVEN FABRIC LAMINATES

[75] Inventors: Terry K. Timmons, Marietta; Steve R. Stopper, Doraville, both of Ga.; Norman K. Fox, Appleton, Wis.; Dennis S. Everhart, Alpharetta, Ga.; William Conn, Stone Mountain, Ga.; Lori A. Morell, Alpharetta, Ga.

[73] Assignee: Kimberly-Clark Corporation, Neenah, Wis.

[21] Appl. No.: 501,202

[22] Filed: Mar. 29, 1990

Related U.S. Application Data

[63] Continuation-in-part of Ser. No. 404,804, Sep. 8, 1989, abandoned.

[51] Int. Cl.⁵ .............................................. B32B 27/44
[52] U.S. Cl. .................................... 428/198; 128/849; 428/171; 428/284; 428/286; 428/296; 428/297; 428/298; 428/903
[58] Field of Search ............... 428/171, 198, 296, 284, 428/903, 286, 297, 298; 128/849

[56] References Cited

U.S. PATENT DOCUMENTS

| | | | |
|---|---|---|---|
| 3,322,607 | 5/1967 | Jung | 161/67 |
| 3,338,992 | 8/1967 | Kinney | 264/24 |
| 3,341,394 | 9/1967 | Kinney | 161/72 |
| 3,502,538 | 3/1970 | Petersen | 161/150 |
| 3,502,763 | 3/1970 | Hartmann | 264/210 |
| 3,542,615 | 11/1970 | Dobo et al. | 156/181 |
| 3,686,385 | 8/1972 | Rohn | 264/164 |
| 3,692,618 | 9/1972 | Dorschner | 161/72 |
| 3,841,953 | 10/1974 | Lohkamp | 161/150 |
| 3,849,241 | 11/1974 | Butin et al. | 161/169 |
| 3,909,009 | 9/1975 | Cvetko et al. | 274/37 |
| 3,914,497 | 10/1975 | Kanehira et al. | 428/288 |
| 4,041,203 | 8/1977 | Brock et al. | 428/157 |
| 4,209,563 | 6/1980 | Sisson | 428/288 |
| 4,211,819 | 7/1980 | Kunimune et al. | 428/374 |
| 4,340,563 | 7/1982 | Appel et al. | 264/518 |
| 4,412,016 | 10/1983 | Fukui et al. | 523/206 |
| 4,451,589 | 5/1984 | Morman et al. | 523/124 |
| 4,579,130 | 4/1986 | Coffman | 131/332 |
| 4,797,318 | 1/1989 | Brooker et al. | 428/283 |
| 4,818,597 | 4/1989 | Da Ponte et al. | 428/171 |
| 4,842,922 | 6/1989 | Krupp et al. | 428/198 |

FOREIGN PATENT DOCUMENTS

| | | | |
|---|---|---|---|
| 803714 | 1/1969 | Canada | 28/5 |
| 0006263 | 1/1980 | European Pat. Off. | |
| 0192897 | 5/1989 | European Pat. Off. | |
| 1902573 | 10/1972 | Fed. Rep. of Germany | 161/150 |

OTHER PUBLICATIONS

NRL Report 4364, Manufacture of Superfine Organic Fibers May 24, 1954, Wente, E. L. Boone, and C. D. Fluharty.

NRL Report 5265, An improved Device For the Formation of Superfine, Thermoplastic Fibers, Feb. 11, 1959, Wente, Boone, Fluharty.

Primary Examiner—James J. Bell
Attorney, Agent, or Firm—William D. Herrick

[57] ABSTRACT

There is disclosed a nonwoven fabric laminate formed from an olefin copolymer, olefin terpolymer, or a blend of olefin polymers. Particularly, the improved fabric laminate is formed from a polymer having a crystallinity of less than 45% and preferably between 31–35% and most preferably about 32%. The fabric laminates formed from layers that are spun-bonded or melt-blown have improved characteristics including higher tear strength, greater tensile energy, greater abrasion resistance, better fabric drape and softness, and less particulate emission. There is also disclosed a low particle emission, sterilizable garment for use in clean rooms, paint rooms, and operating rooms.

64 Claims, 5 Drawing Sheets

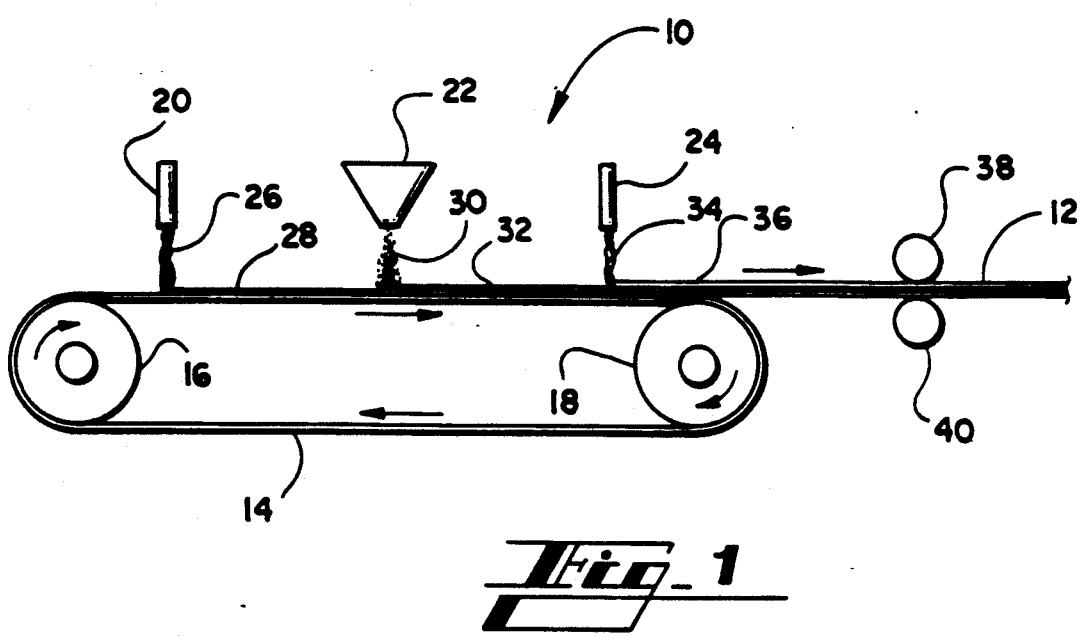
Fig_1
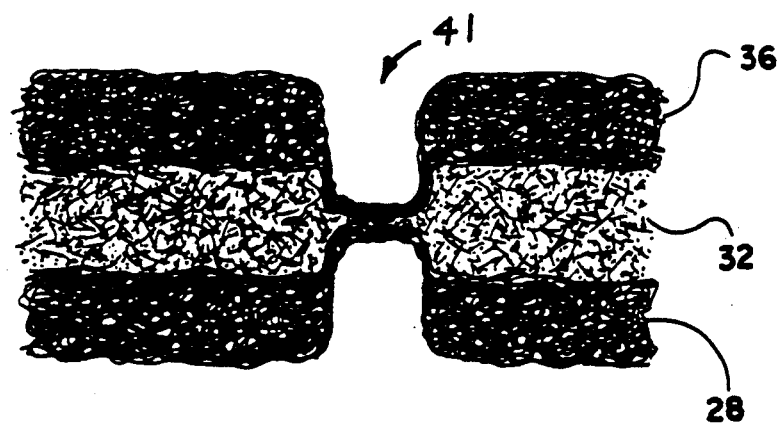
Fig_2

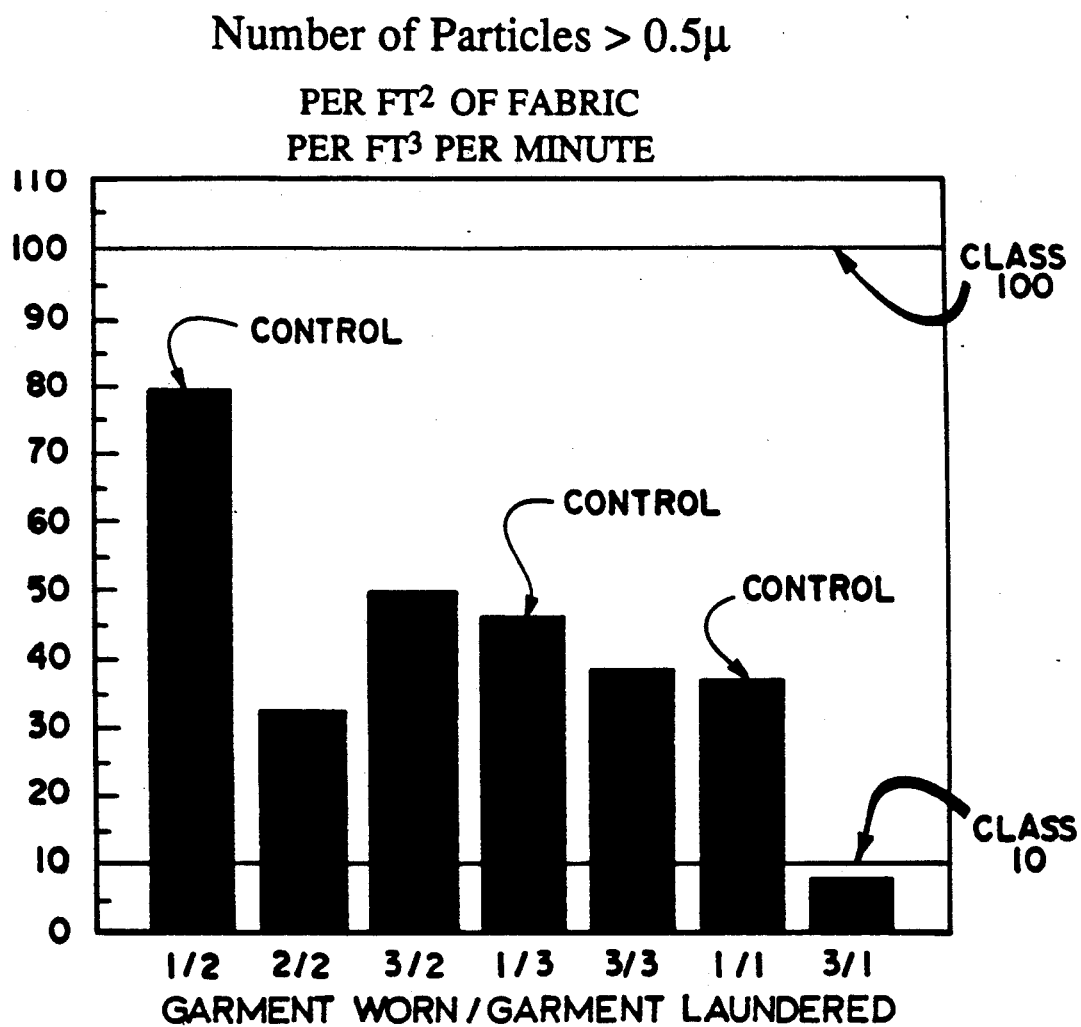
Fig_6

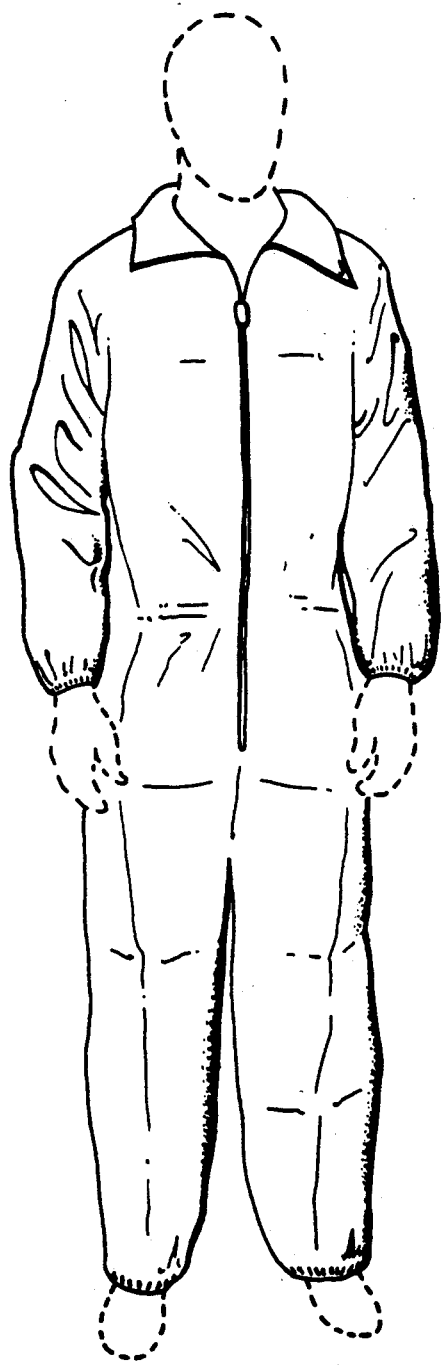
Fig_7

NONWOVEN FABRIC LAMINATES

RELATED CASE

This application is a continuation-in-part of our application Ser. No. 404,804 filed Sep. 8, 1989, is now abandoned.

BACKGROUND OF THE INVENTION

This invention relates generally to disposable fabrics and fabric laminates and more particularly concerns a fabric laminate which has layers that are thermally bonded and are made from a low crystalline olefin copolymer, a low crystalline olefin terpolymer, or a low crystalline blend of olefin polymers. The fabric laminate of the present invention is softer, is stronger, is more abrasion resistant, and has reduced particle emission as compared to current SMS fabric laminates.

Nonwoven fabric laminates are useful for a wide variety of applications. Particularly, nonwoven fabric laminates are useful for wipers, towels, industrial garments, medical garments, medical drapes, sterile wrap, and the like. Fabric laminates, such as spun-bonded/melt-blown/spunbonded (SMS) fabric laminates, made of isotactic polypropylene have achieved widespread use in operating rooms for drapes, gowns, towels, sterile wraps, footcovers, and the like. Such fabric laminates are well-known as shown in U.S. Pat. No. 4,041,203 assigned to Kimberly-Clark Corporation, the assignee of the present invention. For a number of years, Kimberly-Clark has manufactured and sold SMS medical fabric laminates under the marks Spunguard ®, Evolution ®, and Kimguard ®. Such SMS fabric laminates have outside spun-bonded layers which are durable and an internal melt-blown barrier layer which is porous yet which inhibits the penetration of fluids and bacteria through the composite fabric laminate. The layers are thermally bonded together by spot bonding in discrete areas of the fabric.

Generally, such conventional SMS medical fabric laminates are made from layers of spun-bonded and melt-blown polypropylene. Commercially available isotactic polypropylene has a crystallinity of from 45–65% and a relatively narrow melt temperature range. While SMS fabric laminates made from commercial polypropylene exhibit satisfactory attributes in terms of tensile strength, resistance to fluid and bacteria penetration, breathability, and cost, there appears to be advantages to be gained from improving the drape, abrasion resistance, tear strength, and particle emission of the SMS fabric laminates made from polypropylene.

Conventional SMS fabric laminates made of isotactic polypropylene have not achieved widespread use as garments and protective coverings in more demanding clean rooms, particularly sterile clean rooms, and in paint rooms because of the higher requirements for such uses and such SMS fabric laminates tend to emit particles, either particles from the fabric itself or by passage of particles from the wearer to the atmosphere.

SUMMARY OF THE INVENTION

It is therefore an object of the present invention to provide a fabric laminate which is softer, is stronger, is more abrasion resistant, and has reduced particle emission as compared to current fabric laminates that are thermally spot bonded and are made of isotactic polypropylene.

It is particularly an object of the present invention to provide a fabric laminate which has equivalent tensile strength but higher tear strength than current fabric laminates made from polyproylene.

It is further an object of the present invention to provide a fabric laminate having greater extensibility and greater tensile energy than conventional fabric laminates made from polypropylene.

A further object of the present invention is to provide a fabric laminate which has greater abrasion resistance than existing fabric laminates made from polypropylene.

It is also an object of the present invention to provide a fabric laminate having improved fabric drape and softness as compared to fabric laminates made from polypropylene.

It is an object of the present invention to provide a sterile wrap that has enhanced attributes in terms of softness, strength, and abrasion resistance.

It is also an object of the present invention to provide a surgical gown that has enhanced attributes in terms of softness, strength, and abrasion resistance.

It is also an object of the present invention to provide a fabric laminate having reduced particle emission as compared to fabric laminates made from polypropylene.

It is additionally an object of the present invention to provide a protective garment having reduced particle emission for use in clean rooms, particularly sterile clean rooms, and paint rooms.

It is likewise an object of the present invention to provide a protective garment having reduced particle emission which can be sterilized without significant degradation of the low particle emission characteristics of the garment.

The foregoing objectives are accomplished by a fabric laminate in which at least some of the layers are formed from an olefin copolymer, terpolymer, or blends of olefin polymers. The polymers are formulated to produce a polymer having a crystallinity of less than 45%, preferably between 31–35% and most preferably about 32%. The resulting polymer has a broadened melt temperature range which allows for heat bonding of the fibers and filaments at a lower temperature and over a wider range of processing temperatures.

In one embodiment of the present invention, at least one of the layers of the fabric laminate is formed from a random polypropylene copolymer that has been produced by copolymerizing 0.5–5.0% by weight of ethylene randomly in the backbone to yield a polymer that is less crystalline and with a broader melting range than polypropylene itself. A preferred polymer is produced when 3.0% by weight of ethylene is copolymerized with the polypropylene. The resulting copolymer has a crystallinity of 32% and when spun into fibers or filaments and formed into webs produces the advantages recited in the foregoing objectives.

The fabric laminate of the present invention may preferably have all of the layers formed from a polymer having reduced crystallinity although some advantages of the present invention may be realized where less than all of the layers of the fabric laminate are formed of the polymer of reduced crystallinity. Particularly, forming the outside layers of an SMS fabric laminate with a polymer of reduced crystallinity may be advantageous in terms of softness and abrasion resistance, but strength may be reduced because the melting range of the spun-bonded layers may be essentially the same as the melting range of the interior melt-blown layer formed of a polymer having a higher degree of crystallinity. Unless a melt temperature differential of about 10°–40° C. exists between the spun-bonded and melt-blown layers, bonding will not be optimum and strength will be reduced.

The SMS fabric laminate of the present invention is particularly suited for the fabrication of protective garments for use in clean rooms, particularly sterile clean rooms, and paint rooms. Not only does the SMS fabric laminate have superior drape and abrasive qualities, the SMS fabric laminate has superior particle emission characteristics when compared to conventional SMS fabric laminates. As a result, garments fabricated from the SMS fabric laminate of the present invention are particularly suited for clean room environments where airborn particles must be minimized.

Preferably low particle emission garments are constructed from an SMS fabric laminate in which the meltblown layer is formed from high crystalline polypropylene and the spun-bonded layers are formed from a low crystalline copolymer (a C/P/C laminate). The copolymer is formed by copolymerizing 3.2% by weight of ethylene randomly in the backbone of the polypropylene. The resulting copolymer has a crystallinity of less than 32%.

Where garments fabricated with the SMS fabric laminate of the present invention are used in a sterile environment, such as a pharmaceutical manufacturing facility, the SMS fabric laminate is treated with a hindered amine light stabilizer.

Other objects and advantages of the invention will become apparent upon reading the following detailed description and upon reference to the drawings.

BRIEF DESCRIPTION OF THE DRAWINGS

FIG. 1 is a schematic diagram of a forming machine which is used in making the nonwoven fabric laminate of the present invention;

FIG. 2 is a crosssection view of the nonwoven fabric laminate of the present invention showing the layer configuration;

FIG. 6 is a graph showing the particle emission results of clean room laundering test of garments made in accordance with the present invention; and FIG. 7 is a perspective drawing of a clean room garment embodying the present invention.

DETAILED DESCRIPTION OF THE INVENTION

Figure 3:
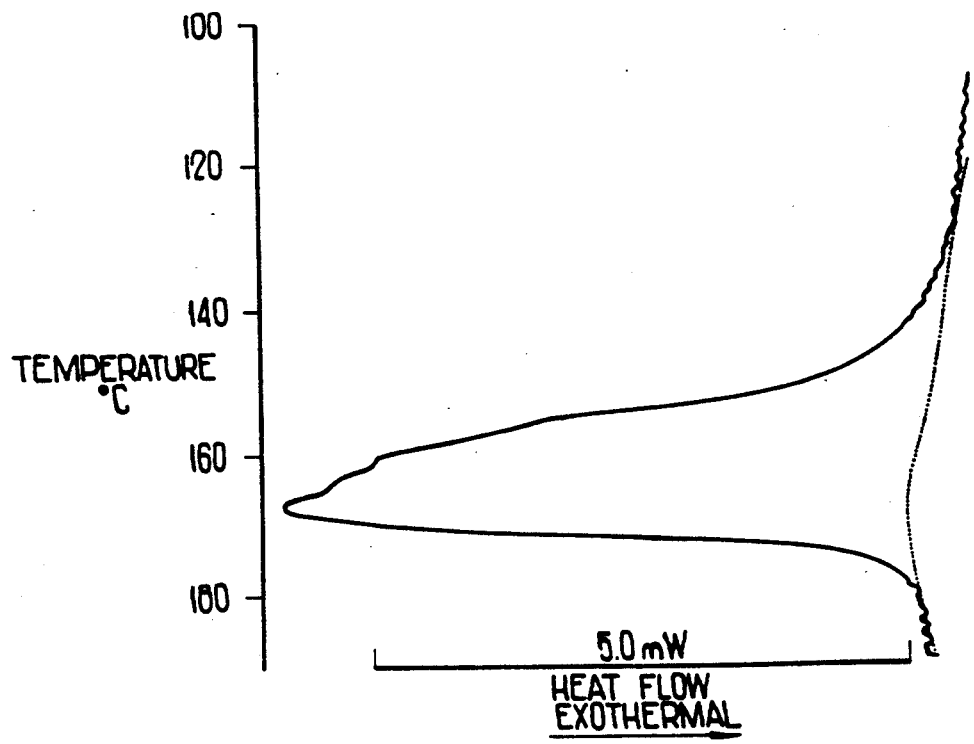
FIG. 3 is a graph showing the melt temperature range of a polymer (polypropylene) used in making fabric laminates in accordance with the prior art.

While the invention will be described in connection with a preferred embodiment and method, it will be understood that we do not intend to limit the invention to that embodiment or method. On the contrary, we intend to cover all alternatives, modifications, and equivalents as may be included within the spirit and scope of the invention as defined by the appended claims.

Turning to FIG. 1, there is shown a schematic of a forming machine 10 which is used to produce an SMS fabric laminate 12 in accordance with the present invention. Particularly, the forming machine 10 consists of an endless foraminous forming belt 14 wrapped around rollers 16 and 18 so that the belt 14 is driven in the direction shown by the arrows. The forming machine 10 has three stations, spun-bond station 20, melt-blown station 22, and spun-bond station 24.

The spun-bond stations 20 and 24 are conventional extruders with spinnerettes which form continuous filaments of a polymer and deposit those filaments onto the forming belt 14 in a random interlaced fashion. The spun-bond stations 20 and 24 may include one or more spinnerette heads depending on the speed of the process and the particular polymer being used. Forming spunbonded material is conventional in the art, and the design of such a spun-bonded forming station is thought to be well within the ability of those of ordinary skill in the art. The nonwoven spun-bonded web 32 is prepared in conventional fashion such as illustrated by the following patents: Dorschner et al. U.S. Pat. No. 3,692,618; Kinney U.S. Pat. Nos. 3,338,992 and 3,341,394; Levy U.S. Pat. No. 3,502,538; Hartmann U.S. Pat. Nos. 3,502,763 and 3,909,009; Dobo et al. U.S. Pat. No. 3,542,615; Harmon Canadian Pat. No. 803,714; and Appel et al. U.S. Pat. No. 4,340,563. Other methods for forming a nonwoven web having continuous filaments of a polymer are contemplated for use with the present invention.

Spun-bonded materials prepared with continuous filaments generally have at least three common features. First, the polymer is continuously extruded through a spinnerette to form discrete filaments. Thereafter, the filaments are drawn either mechanically or pneumatically without breaking in order to molecularly orient the polymer filaments and achieve tenacity. Lastly, the continuous filaments are deposited in a substantially random manner onto a carrier belt to form a web. Particularly, the spunbond station 20 produces spun-bond filaments 26 from a fiber forming polymer. The filaments are randomly laid on the belt 14 to form a spunbonded external layer 28. The fiber forming polymer is described in greater detail below.

The melt-blown station 22 consists of a die which is used to form microfibers 30. The microfibers 30 are randomly deposited on top of the spun-bond layer 28 and form a melt-blown layer 32. The construction and operation of the melt-blown station 22 for forming microfibers 30 and melt-blown layer 32 is considered conventional, and the design and operation are well within the ability of those of ordinary skill in the art. Such skill is demonstrated by NRL Report 4364, "Manufacture of Super-Fine Organic Fibers", by V. A. Wendt, E. L. Boom, and C. D. Fluharty; NRL Report 5265, "An Improved Device for the Formation of Super-Fine Thermoplastic Fibers", by K. D. Lawrence, R. T. Lukas, and J. A. Young; and U.S. Pat. No. 3,849,241, issued Nov. 19, 1974, to Buntin et al. Other methods for forming a nonwoven web of microfibers are contemplated for use with the present invention.

The melt-blown station 22 produces microfine fibers 30 from a fiber forming polymer which will be described in greater detail below. The fibers 30 are randomly deposited on top of spun-bond layer 28 to form a melt-blown internal layer 32. For an SMS medical fabric laminate, for example, the melt-blown barrier layer 32 has a basis weight of preferably about 0.35–0.50 oz./yd.$^2$. For a clean room garment, for example, the melt-blown barrier layer 32 of the SMS fabric laminate has a basis weight of preferably about 0.4 oz./yd.$^2$ to about 0.8 oz./yd.$^2$.

After the internal layer 32 has been deposited by the melt-blown station 22 onto layer 28, spun-bond station 24 produces spun-bond filaments 34 of polymer which are deposited in random orientation on top of the melt-blown layer 32 to produce external spun-bond layer 36. For an SMS medical fabric laminate, for example, the layers 36 and 28 each have a basis weight of preferably from about 0.30 oz./yd.$^2$ to about 1.2 oz./yd.$^2$. For a clean room garment, for example, the layers 36 and 28 of the SMS fabric laminate each have a basis weight of preferably from about 0.3 oz./yd.$^2$ to about 1.0 oz./yd.$^2$.

The resulting SMS fabric laminate web 12 (FIG. 2) is then fed through bonding rolls 38 and 40. The surface of the bonding rolls 38 and 40 are provided with a raised pattern such as spots or grids. The bonding rolls are heated to the softening temperature of the polymer used to form the layers of the web 12. As the web 12 passes between the heated bonding rolls 38 and 40, the material is compressed and heated by the bonding rolls in accordance with the pattern on the rolls to create a pattern of discrete areas, such as 41 shown in FIG. 2, which areas are bonded from layer to layer and are bonded with respect to the particular filaments and/or fibers within each layer. Such discrete area or spot bonding is well-known in the art and can be carried out as described by means of heated rolls or by means of ultrasonic heating of the web 12 to produced discrete area thermally bonded filaments, fibers, and layers. In accordance with conventional practice described in Brock et al. U.S. Pat. No. 4,041,203, it is preferable for the fibers of the melt-blown layer in the fabric laminate to fuse within the bond areas while the filaments of the spun-bonded layers retain their integrity in order to achieve good strength characteristics.

A typical bonding pattern designated "H&P" has square pin bonding areas wherein each pin has a side dimension of 0.038 in., a spacing of 0.070 in. between pins, and a depth of bonding of 0.023 in. The resulting pattern has a bonded area of about 29.5%. Another typical bonding pattern designated "714" has square pin bonding areas wherein each pin has a side dimension of 0.023 in., a spacing of 0.062 in. between pins, and a depth of bonding of 0.033 in. The resulting pattern has a bonded area of about 15%. Another typical bonding pattern is the "EHP" bond pattern which produces a 15% bond area with a square pin having a side dimension of 0.037 in., a pin spacing of 0.097 in., and a depth of 0.039 in. Typically, the percent bonding area varies from around 10% to 30% of the area of the fabric laminate web 12. As is wellknown in the art, the spot bonding holds the laminate layers together as well as imparts integrity to each individual layer by bonding filaments and/or fibers within each layer.

While the particular bonding pattern does not form any part of the present invention, the ability of the polymer filaments and fibers to bond within the discrete bond areas is important to providing a fabric laminate web 12 which has a high tear strength, high tensile energy, is abrasion resistant, has reduced particle emissions, and still has increased fabric drape and softness. In that regard, we have found that fabric laminates having layers formed from olefin copolymers, terpolymers, and blends of polymers having a crystallinity less than 45% provide improved thermal bonding and therefore improved fabric characteristics even through such polymers produce fibers with lower tenacity and lower modulus than those fibers formed from polypropylene. More preferably, at least some of the layers of the fabric laminate are formed from an olefin copolymer, an olefin terpolymer, or blend of olefin polymers having a crystallinity between 31-35%. Even more preferably, at least some of the layers of the fabric laminate are formed from an olefin copolymer, olefin terpolymer or blend of olefin polymers having a crystallinity of about 32%.

In order to achieve such a reduced crystallinity polymer for forming a layer for a fabric laminate, we have found that copolymerizing 0.5 to 5.0% by weight of ethylene randomly in the backbone of polypropylene produces a copolymer which is especially useful for spun-bonded webs and combinations of spun-bonded and melt-blown webs for use in producing a fabric laminate. Particularly, such a copolymer finds usefulness in producing SMS fabric laminates.

Figure 4:
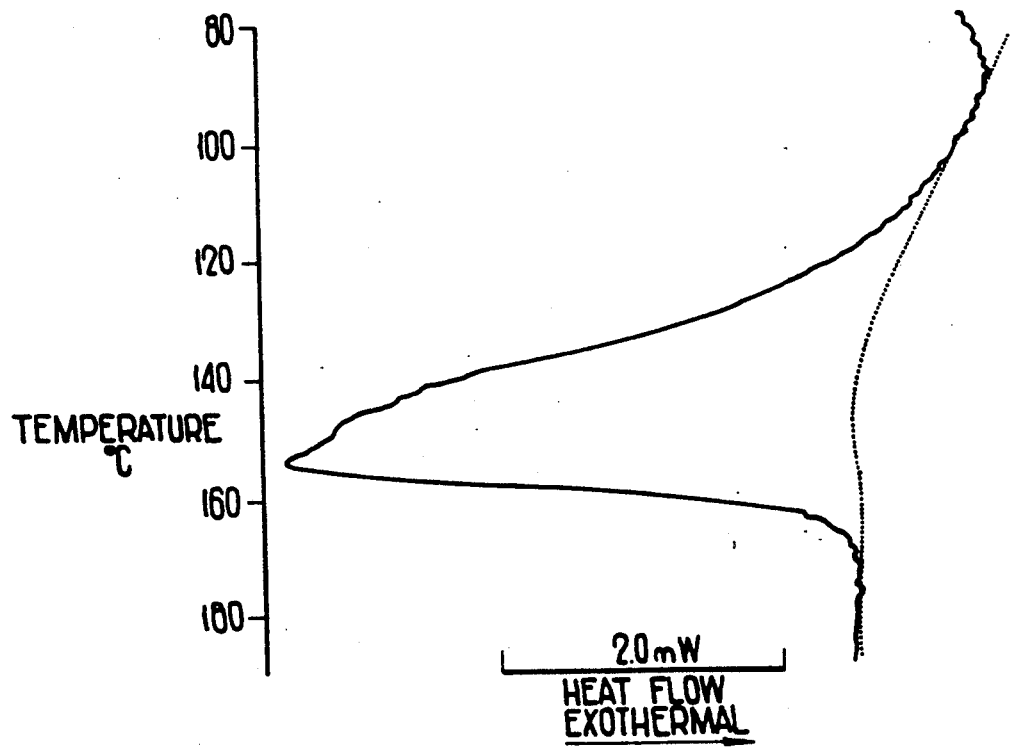
FIG. 4 is a graph showing the melt temperature range of a copolymer used in making fabric laminates in accordance with the present invention.

By using an olefin copolymer, olefin terpolymer, or blend of olefin polymers having a reduced crystallinity for producing laminate layers, the resulting modified thermoplastic polymer has a broadened melting range which achieves bonding at a lower spot bonding temperature and provides bonding over a broader range of temperatures encountered during the spot bonding process. With reference to FIGS. 3 and 4, one can see graphically the broadened melt temperature range that the propylene copolymer (3% ethylene) has (FIG. 4) as compared to higher crystallinity polypropylene (FIG. 3). For example, the polypropylene melts over a very narrow range of about 150°-170° C. while the propylene copolymer (3% ethylene) melts over a broader and lower temperature range of about 125°-160° C. It is believed that the reduced crystallinity of the copolymer, terpolymer, or polymer blend results not only in a fabric that is easier to process because of the broadened melt temperature range but also a polymer which bonds more securely without damage to the fibers than the higher crystallinity polymers, such as polypropylene, which are customarily used in manufacturing spun-bonded and meltblown webs which are used to make SMS fabric laminates. Moreover, the copolymer in the spun-bonded layer makes the spun-bonded layer more compatible in bonding temperature with the interior melt-blown layer, even where the melt-blown layer is formed from a polymer of high crystallinity such as polypropylene. Consequently, the resulting bonding is more secure and the likelihood of pinholes occurring is reduced.

The fabric laminates of the present invention with improved strength, softness and drape, abrasion resistance, and particle emission are useful in a number of applications. For example, SMS fabric laminates embodying the present invention can be converted into surgical gowns, surgical drapes, sterile wrap, and clean room garments including sterilizable clean room garments.

The present invention is illustrated by comparison of SMS fabric laminates formed of unmodified high crystallinity polypropylene to SMS fabric laminates having at least some layers formed from a copolymer of 3% by weight of ethylene copolymerized randomly in the backbone of the polypropylene.

EXAMPLE 1

In order to evaluate the effect of forming the layers of an SMS fabric laminate using a copolymer with reduced crystallinity, such as a propylene copolymer (3% ethylene), six samples of SMS fabric laminates were prepared and tested. The six samples are shown in Table 1 below which records their layer composition and the various tests that demonstrate the superiority of the fabric laminates formed from the copolymer in terms of higher tear strength, higher tensile energy, greater abrasion resistance, and increased fabric drape and softness.

Fabric laminate Samples 2, 4, and 6 are SMS fabric laminates which were prepared using an unmodified polypropylene polymer, particularly Exxon PD3125 for the spun-bonded layers and Exxon 3214 plus peroxide for the melt-blown layer. Such polypropylene polymers are manufactured and sold by Exxon Chemical Company of Baytown, Tex. The layers were bonded at a temperature of 290° F.

Fabric laminate Samples 1, 3, and 5 were prepared using the same process parameters as Samples 2, 4, and 6 respectively except that propylene copolymer (3% ethylene) was used for forming the layers instead of polypropylene and the bonding temperature was reduced. The copolymer is manufactured by Shell Oil Company and designated Shell WRS 6-144 3% ethylene. The copolymer is produced by copolymerizing propylene with 3% by weight of ethylene.

As a result of the broadened melt temperature range of the copolymer, a lower bonding temperature, between 275°-280° F., was used to bond the layers of the SMS fabric laminate made from the copolymer. Consequently, the only difference between the preparation of Sample 1 and Sample 2 was the use of the 3% copolymer instead of unmodified polypropylene and a lower bonding temperature. Likewise the preparation of Sample 3 and Sample 4 and the preparation of corresponding Sample 5 and Sample 6 varied only in terms of the polymer used and the bonding temperature.

ounces per square yard and is shown in the "Basis Weight" line of Table 1. Basis weight was measured in accordance with Federal Test Method (FTM) 191A-5.

The grab tensile strength in pounds was measured in both the machine direction and cross direction ("MD/CD"). The grab tensile strength was measured in accordance with FTM 191A, Method 5100. It can be seen from Table 1 that the grab tensile strength for the corresponding copolymer and polypropylene samples is essentially the same thereby indicating that the copolymer fiber and filaments with their lower tenacity and lower modulus do not, as expected, reduce the grab tensile strength of the fabric laminate.

Elongation as a percentage was measured in both the machine and the cross-direction. As can be seen by comparing Samples 1 and 2, Sample 1, the copolymer fabric laminate sample, has substantially better elongation properties than that of the polypropylene fabric laminate sample, Sample 2. With respect to Samples 5 and 6, the elongation is essentially the same. The elongation was measured in accordance with FTM 191A, Method 5100.

With respect to peak energy, it can be seen that the copolymer fabric laminate Samples 1 and 5, have a substantial advantage over the polypropylene fabric laminate Samples 2 and 6 in terms of the peak energy characteristics. The peak energy was measured in accordance with FTM191A, Method 5100.

With regard to trapezoidal tear strength, measured in pounds in both the machine and cross-direction, it can be seen that the copolymer fabric laminate Samples 1, 3, and 5 enjoy a substantial advantage over the respective polypropylene fabric laminate Samples 2, 4, and 6. Trapezoidal tear was measured in accordance with

TABLE 1

| | Sample 1 | Sample 2 | Sample 3 | Sample 4 | Sample 5 | Sample 6 |
|---|---|---|---|---|---|---|
| Polymer | C/C/C | P/P/P | C/C/C | P/P/P | C/C/C | P/P/P |
| Pattern/fiber shape | EHP/ROUND | EHP/ROUND | EHP/ROUND | EHP/ROUND | 714 ROUND | 714 ROUND |
| Calender Temp (°F.) | 280 | 292 | 278 | 292 | 275 | 290 |
| Basis Weight (osy) | 1.58 | 1.59 | 1.42 | 1.40 | 1.49 | 1.42 |
| Grab Tensile MD/CD (lbs) | 22.9/20.9 | 21.3/20.9 | 19.8/19.2 | 21.7/20.2 | 23.1/19.2 | 19.5/16.1 |
| Elongation MD/CD (%) | 68.6/80.8 | 48.6/57.9 | — | — | 73/87 | 76/75 |
| Peak Energy MD/CD (lbs) | 29.1/28.7 | 19.3/20.4 | 23.0/27.1 | — | 40.5/39.2 | 39.1/29.8 |
| Trap Tear MD/CD (lbs) | 10.9/9.4 | 8.8/8.7 | 9.1/8.1 | 8.8/7.7 | 10.5/9.6 | 9.9/7.5 |
| Taber Abrasion *Pin/Anvil (cycles) | 89/60 | 53/39 | 87/22 | 51/24 | 52/29 | 11/8 |
| Coefficient of Friction (fabric to fabric) | 0.485 | 0.395 | 0.543 | — | 0.53 | 0.45 |
| SST Softness (higher is softer) | 67 | 29 | 87 | 33 | 96 | 86 |
| Drape Stiffness MD/CD | 3.3/2.5 | 3.3/2.7 | 3.1/2.4 | — | 3.4/2.1 | 3.7/2.3 |

*Taber abrasion of 50 replicates/sample

With respect to Table 1 above, the "Polymer" line of Table 1 shows that Sample 1 is a three layer SMS fabric laminate using the propylene copolymer (3% ethylene) ("C/C/C") for each of the layers in the fabric laminate. By the same token, the Table shows that Sample 2 is a three layer SMS fabric laminate made with unmodified polypropylene ("P P P"). Sample 2 was formed by the same process as Sample 1 except that a higher bonding temperature was used to bond the polypropylene layers of the fabric laminate.

The "pattern/fiber shape" line of Table 1 indicates that the standard spot bonding pattern "EHP" was used for Samples 1-4. For Samples 5 and 6, the "714" bonding pattern was used. The term "round" for each of the samples indicates the cross-sectional shape of the fiber which results from using a spinning orifice that is round. The basis weight of each sample was measured in FTM 191A, Method 5450.

The abrasion of the fabric laminate was measured in accordance with the Taber Abrasion Test and shows that for respective samples the copolymer fabric laminates are more abrasion resistant than the polypropylene fabric laminates. The abrasion resistance was measured in accordance with FTM 191A, Method 5306 at 50 replications per sample.

The softness of the respective copolymer fabric laminate samples as compared to the polypropylene fabric laminate samples is remarkably improved as indicated by the higher index number. The softness was measured by an inhouse procedure similar to INDA Std. Test IST 90.0-75 (R-82).

The drape stiffness measured in centimeters in both the machine and cross-direction is less for the copolymer fabric laminate samples as compared to the respective polypropylene fabric laminate samples thereby indicating that the copolymer fabric laminates are more drapeable. Drape stiffness was measured in accordance with FTM 191A, Method 5206.

In summary with respect to strength and elongation, the copolymer fabric laminates consistently are 10–30% higher in elongation and peak energy than the polypropylene fabric laminates due to the lower crystallinity and better bonding of the fibers and filaments. The increased toughness is also reflected in the higher trapezoidal tear values.

There is no significant difference in grab tensile strength. The lower tensile strength which was expected for the less crystalline copolymer was likely overshadowed by the better bonding of the copolymer during the spot bonding process. Abrasion resistance, according to the Taber results, is consistently 40% greater for the copolymer fabric laminates as compared to the polypropylene fabric. The failure mechanism is the same for the copolymer fabric laminates as well as for the polypropylene fabric laminates with the EHP pattern. Both fabric laminates show equal amounts of fiber breakage and fibers pulled from the bond points. With the 714 pattern, the failure mechanism is predominantly fiber pulled from bonding points rather than the fiber breakage. The better abrasion resistance for the copolymer is attributed to better bonding and more flexible spun-bonded fibers.

With regard to the tactile properties for the fabric laminates, the copolymer fabric laminates appear better than the polypropylene fabric laminates. Physical and sensory panel evaluation reveals that the copolymer fabric laminates have slightly better drape, higher fabric to fabric friction, and higher drag against the skin than polypropylene fabric laminates. The copolymer fabric laminates produce a slight increase in fabric softness, and the sensory panel consistently judged the copolymer fabric laminates softer and less abrasive than polypropylene fabric laminates.

While work was done using the propylene copolymer (3% ethylene) described above, it is believed that the useful range for the ethylene is as stated between 0.5–5.0% by weight of ethylene. We have found, however, that as the ethylene content approaches 5.0% the fabric laminates begin to lose tensile strength although the fabric laminates seem to retain their other desirable attributes. Also at 5.0% ethylene the copolymer becomes difficult to process because of its adhesive characteristics.

EXAMPLE 2

In another set of tests, two conventional fabric laminates and two fabric laminates in accordance with the present invention were made and tested. The four samples are shown in Table 2 below which records their composition and the various tests that demonstrate the superiority of the fabric laminate formed from layers of copolymer in terms of higher tear strength, higher tensile energy, greater abrasion resistance, and increased fabric drape and softness.

Fabric laminates Samples 7 and 8 are SMS fabric laminates which were prepared using an unmodified polypropylene polymer, particularly Exxon PD3125 for the spun-bonded layers and Exxon 3214 plus peroxide for the melt-blown layer.

Samples 9 and 10 are fabric laminates which were prepared using essential the same process parameters as Samples 7 and 8 except that propylene copolymer (3% ethylene) was used for forming all of the layers instead of polypropylene and the bonding temperature was reduced. The copolymer was Shell WRS 6-144 3% ethylene. Samples 7 and 8 also differ from Samples 9 and 10 as a result of the use of a different spot bonding pattern and small variations in basis weight. A lower bonding temperature was used for the copolymer fabric laminates, Samples 9 and 10, because of the broader softening temperature range exhibited by the copolymer. The results are reported in Table 2:

TABLE 2

|  | Sample 7 | Sample 8 | Sample 9 | Sample 10 |
| --- | --- | --- | --- | --- |
| Pattern-Material | EHP-P/P/P | EHP-P/P/P | 714-C/C/C | 714-C/C/C |
| Fiber Shape | round | round | round | round |
| Basis Wt. Total (MB) | 1.4 (.35) | 1.59 (.55) | 1.55 (.43) | 1.7 (.48) |
| Grab Tensile Strength (lbs) MD/CD | 19.54/16.55 | 22.25/18.35 | 22.48/19.70 | 24.91/21.11 |
| Grab Peak Energy (in-lbs) MD/CD | 14.89/14.59 | 20.49/16.26 | 24.02/22.48 | 24.67/24.52 |
| Elongation (%) MD/CD | 40.41/53.76 | 43.03/50.82 | 59.88/69.35 | 55.59/69.26 |
| Trapezoidal Tear Strength (lbs) MD/CD | 6.68/5.74 | 7.37/8.11 | 9.15/7.67 | 8.78/7.80 |
| Trapezoidal Tear Strength Post Irradiation (lbs) MD/CD | 6.68/5.74 | 7.37/8.11 | 7.32/6.14 | 7.22/6.40 |
| Taber Abrasion (cycles) Face/Anvil | 20/12 | 15/11 | 14/8 | 14/6 |
| SST Softness (mm) | 67.5 | 51.6 | 61.5 | 53.6 |
| Drape Stiffness (cm) MD/CD | 3.8/2.1 | 3.5/2.1 | 3.6/2.4 | 3.6/2.4 |

With reference to Table 2, the first line entitled "Pattern-Material" indicates the bonding pattern, either "EHP" or "714", and the material, polypropylene or the copolymer, used in each of the layers. For example, Sample 7 is a three layer SMS fabric laminate having all three layers made of a high crystalline polypropylene whereas Sample 9 is a three layer SMS fabric laminate with all three layers made from a propylene copolymer (3% ethylene). The next line of Table 2 describes the shape of the fiber or filament. The line entitled "Basis Weight Total (MB)" shows the total basis weight of the three layer laminate and the basis weight of the internal melt-blown layer in parenthesis. For example, in Sample 7 the total fabric laminate has a basis weight of 1.4 oz/yd$^2$ with the internal melt-blown layer having a basis weight of 0.35 oz/yd$^2$. Consequently, each spun-bonded exterior layer is just slightly greater than 0.50 oz/yd$^2$.

With regard to the grab tensile strength, it can be seen from Table 2 that the grab tensile strength for the copolymer and polypropylene fabric laminate samples is essentially the same thereby indicating that using the copolymer does not, as expected, reduce the grab tensile strength of the fabric laminate. It should be appreciated, however, that direct comparisons between the polypropylene fabric laminates and the copolymer fabric laminates listed in Table 2 may be overshadowed by the use of the different bonding patterns for the polypropylene fabric laminates and the copolymer fabric laminates. In Table 2 it also appears that the basis weight might also affect strength.

With respect to peak energy, it can be seen that the copolymer fabric laminates, Samples 9 and 10, possess higher peak energy than the polypropylene fabric laminates, Samples 7 and 8. Again, those differences may in part be masked by the use of the different bonding patterns.

laminate, some of the advantages of the present invention can be achieved by using the copolymer, terpolymer, or blend in less than all of the layers of the fabric laminate.

Two additional fabric laminate Samples 11 and 12 were prepared and tested. The two samples, Samples 11 and 12, are shown in Table 3 below.

Sample 11 is an SMS fabric laminate having the spunbond layers formed from the propylene copolymer (3% ethylene) and the interior melt-blown layer formed from high crystalline polypropylene. Sample 12 is an SMS fabric laminate with all three layers formed from high crystalline polypropylene as previously described in connection with Example 1. The polypropylene used in the melt-blown layers of both samples was Himont PF-015 manufactured by Himont USA, Inc., Wilmington, Del. The spunbonded layers in Sample 12 are formed from Himont PC 973. The composition of the two samples and test results are reported in Table 3:

TABLE 3

|  |  | Sample 11 | Sample 12 |
|---|---|---|---|
| Pattern-Material |  | 714-C/P/C | 714-P/P/P |
| Fiber shape |  | round | round |
| Basis Wt. Total (MB) | Test History | 1.7 (0.40) | 1.7 (0.40) |
| Grab Tensile Strength | At time of mfg. | 19.2/20.0 | 23.0/21.8 |
| (lbs) MD/CD | 3 wks after mfg. | 20.6/19.2 | 23.8/21.6 |
| Grab Peak Energy (in-lbs) MD/CD | 3 wks after mfg. | 17.9/18.7 | 17.0/16.2 |
| Trap Tear (lbs) MD/CD | At time of mfg. | 10.3/7.3 | 8.0/8.0 |
|  | 2 wks after mfg. | 8.7/7.8 | 8.3/7.0 |
| Taber (cycles to endpt.) | 3 wks after mfg. | 83/24 | 26/9 |
| Crush Energy (g · mm) | At time of mfg. | 3437 | 4240 |
|  | 2 wks after mfg. | 4200 | 4860 |
| SST Softness (mm) | 2 wks after mfg. | 53 | 45 |

With respect to elongation, it can be seen that the copolymer fabric laminates, Samples 9 and 10, have a greater percentage elongation than the polypropylene fabric laminates, Samples 7 and 8. Again, the true value of the difference may be masked by the different bonding patterns used.

With respect to trapezoidal tear strength, it can be seen that the copolymer fabric laminates are stronger or at the very least comparable to the polypropylene fabric laminates.

With respect to abrasion, the copolymer fabric laminates, Samples 9 and 10, do not perform as well as the polypropylene fabric laminates either with respect to the Taber Abrasion Test. It is believed that the poor abrasion performance is due to the difference in bonding pattern used for the copolymer fabric laminates and for the polypropylene fabric laminates. In any event, the loss of abrasion resistance is not so great as to make a substantial difference in performance for the copolymer fabric laminates.

With regard to softness and drape, it can be seen that the copolymer fabric laminates, Samples 9 and 10, are of equal softness to the polypropylene fabric laminates with respect to the SST softness test and the drape stiffness test.

In summary, the fabric laminates, Samples 9 and 10, consisting of layers formed from the copolymer have improved peak energy, improved tear strength, and comparable abrasion resistance to the conventional polypropylene fabric laminates, Samples 7 and 8.

EXAMPLE 3

While the fabric laminate samples made in accordance with the present invention and described above used the copolymer for all of the layers of the fabric It was observed that the grab tensile strength of the SMS fabric of Sample 11 was lower than that of SMS fabric having all three layers formed of the propylene copolymer (3% ethylene) and lower than that of conventional SMS fabric having all three layers formed of propylene polymer. It is believed that this reduction in the grab tensile strength may be due to the fact that the softening temperature of the propylene copolymer (3% ethylene) used in the spun-bonded layers is lower than that of the propylene polymer. Consequently, the filaments in the spun-bonded layers may have fused excessively in the bond areas thus leading to the reduced strength of the fabric laminate.

With reference to Table 3, Sample 11, as predicted because of the reduced softening temperature differential, has reduced grab tensile strength as compared to the conventional polypropylene fabric laminate, Sample 12. The grab peak energy of Sample 11, however, is essentially the same as the grab peak energy for the conventional fabric laminate, Sample 12, because the higher elongation offsets the reduced tensile strength. The trapezoidal tear strength of Sample 11 made in accordance with the present invention is greater than the trapezoidal tear strength for conventional Sample 12.

Sample 11, also, outperforms the conventional Sample 12 in terms of abrasive resistance as shown by the Taber Abrasion Test.

With regard to softness, Sample 11, also outperformed the conventional Sample 12 in terms of the SST Softness Test.

As previously indicated, the fabric laminates of the present invention have reduced particle emissions when strained or flexed when compared to the particle emissions from conventional fabric laminates formed from isotactic polypropylene fibers and filaments. SMS fabric laminates made in accordance with the present invention emit up to fifty times fewer particles greater than 0.3 microns in diameter when compared to a conventional SMS fabric laminate formed of isotactic polypropylene. Consequently the fabric laminates of the present invention are particularly useful for making clean room garments.

Clean rooms are classified according to the number of particles of a particular size per cubic foot of air. Federal Standard 209D (FED-STD-209D) provides a particle distribution in accordance with the following Table 4 for the classification of clean rooms:

TABLE 4

| Class | Measured Particle Size (Micrometers) | | | | |
|---|---|---|---|---|---|
| | 0.1 | 0.2 | 0.3 | 0.5 | 5.0 |
| 1 | 35 | 7.5 | 3 | 1 | NA |
| 10 | 350 | 75 | 30 | 10 | NA |
| 100 | NA | 750 | 300 | 100 | NA |
| 1,000 | NA | NA | NA | 1,000 | 7 |
| 10,000 | NA | NA | NA | 10,000 | 70 |
| 100,000 | NA | NA | NA | 100,000 | 700 |

(NA. - not applicable)

EXAMPLE 4

In order to demonstrate the improved particle emissions characteristics of fabric laminates made in accordance with the present invention, four SMS fabric laminate samples were prepared and tested. The results are recorded in Table 5. Two samples, Samples 13 and 14, are conventional SMS fabric laminates prepared from isotatic polypropylene. Particularly, Sample 13 is a 1.8 oz/yd$^2$ SMS fabric laminate having its layers bonded with an EHP bond pattern. Sample 14 is a 1.5 oz/yd$^2$ SMS fabric laminate which likewise has been bonded with an HP bond pattern.

Two samples made in accordance with the present invention, Samples 15 and Samples 16, were made using a propylene copolymer (3.2% ethylene) for the external spunbonded layers. The internal melt-blown layer was formed from isotactic polypropylene. Particularly, Sample 15 is a 1.8 oz/yd$^2$ SMS fabric laminate (C/P/C) bonded with an EHP bonding pattern. Sample 16 is a 1.7 oz/yd$^2$ SMS fabric laminate (C/P/C) bonded with a 714 bonding pattern.

The samples were all laundered in accordance with the requirements of the Recommended Practices of the Institute of Environmental Sciences October, 1987, IES-RP-CC-00387-T in a class 10 clean room (FED-STD-209D) so that particles on the samples left over from the manufacturing process would not skew the test results. The laundered samples were tested both using the Helmke Drum Test carried out in accordance with IES-RP-CC-00387-T and the Climet Lint Test carried out in accordance with INDA Std. Test 160.0-83. The results are tabulated in Table 5 below:

TABLE 5

| | Sample 13 (Sample 17 Table 6) | Sample 14 (Sample 18 Table 6) | Sample 15 (Sample 20 Table 6) | Sample 16 (Sample 19 Table 6) |
|---|---|---|---|---|
| Material | P/P/P | P/P/P | C/P/C | C/P/C |
| Basis Weight | 1.8 | 1.5 | 1.8 | 1.7 |
| Bond Pattern | EHP | HP | EHP | 714 |
| Helmke Particle Emission (Particles/ft$^2$ of fabric laminate/ft$^3$/minute) | | | | |
| >0.3 microns | 247 ± 77 | NT | 5 ± 2 | 12 ± 5 |
| >0.5 microns | 182 ± 62 | 98 ± 48 | 3 ± 2 | 9 ± 3 |
| Climet Lint (Total Particles/ft$^2$) Test Time (min): | | | | |
| 0.6 | | 13 | 14 | 3 | 3 |
| 5.0 | 383 | NT | 58 | NT |
| 8.0 | 966 | NT | 175 | NT |
| 10.0 | 1700 | NT | 447 | NT |

As can be seen from Table 5, it is clear that fabric laminates made using the propylene copolymer (3.2% ethylene) produced substantially less particle emissions than the conventional fabric laminates formed from isotactic polypropylene filaments and fibers.

It appears that the advantages of low particle emission can be achieved by using a copolymer for the external spunbonded layers of an SMS fabric laminate which copolymer results from copolymerizing 0.5 to 5.0% by weight of ethylene randomly in the backbone of polypropylene. For low particle emission SMS fabric laminates a 3.2% ethylene copolymer is preferred. It has also been found that blends of olefins are useful for forming the external spun-bonded layers of a low particle emission SMS fabric laminate. Particularly, it has been found that a blend of polypropylene and polybutylene for forming the spun-bonded layers of an SMS fabric laminate can produce a low emission fabric laminate as compared to conventional polypropylene SMS fabric laminates. The blend of polypropylene and polybutylene can be in the range of from 5 to 20% by weight of polybutylene with 5% by weight of polybutylene preferred.

The adaptability of the inventive copolymer and polymer blends to SMS fabric laminates for clean room garments is further shown by the following example.

EXAMPLE 5

Figure 5:
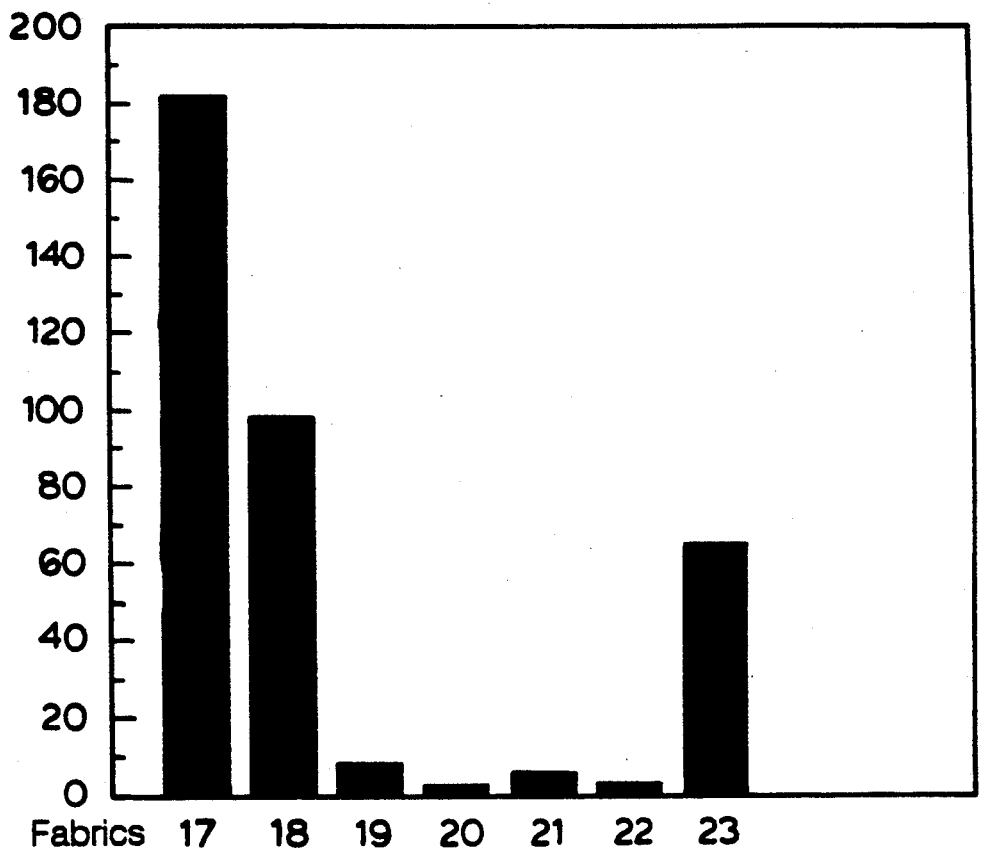
FIG. 5 is a graph showing the particle emission results of a Helmke Drum Test for various fabrics.

In order to demonstrate the improved particle emissions characteristics of fabric laminates made in accordance with the present invention, seven SMS fabric laminate samples (Samples 17 through 23) were prepared and tested by means of the Helmke Drum Test. The characteristics of the samples and the results of the Helmke Drum Test are set forth in Table 6 below and illustrated in FIG. 5.

Two samples, Samples 17 and 18, are conventional SMS fabric laminates prepared from isotatic polypropylene. Sample 17 (which is in fact five separate samples) is an SMS fabric laminate sold by Kimberly-Clark and converted into garments under the trademark KleenGuard ®. The SMS fabric laminate has a total basis weight of 1.80 oz/yd², with the internal melt-blown layer having a basis weight of 0.60 oz/yd². Sample 18 (which was in fact five separate samples) is an SMS fabric laminate sold by Kimberly-Clark under the trademark KleenGuard ® and has a total basis weight of 1.50 oz/yd², with the internal melt blown layer having a basis weight of 0.45 oz/yd².

Samples 19 through 22 were made in accordance with the present invention. Each of the Samples 19 through 22 is an SMS fabric laminate. The external layers of Samples 19 through 22 are spun-bonded and formed of a copolymer resulting from copolymerizing 3.2% by weight of ethylene randomly in the backbone of polypropylene. The internal melt-blown layer of each sample is formed of isotactic polypropylene. Sample 19 (in fact five samples) has a basis weight of 1.75 oz/yd², with the internal melt-blown layer having a basis weight of 0.42 oz/yd². Sample 20 (in fact five samples) has a total basis weight of 1.80 oz/yd², with the melt-blown internal layer having a basis weight of 0.60 oz/yd². Sample 21 (in fact five samples) has a total basis weight of 1.75 oz/yd², with the melt-blown internal layer having a basis weight of 0.42 oz/yd². Sample 22 (in fact three samples) is the same as Sample 21 except that Sample 22 has been sterilized by subjecting the sample to gamma radiation in accordance with standard practices specified by the FDA. In order to make the SMS fabric laminate stable for sterilization, the spun-bonded layers are treated with a hindered amine. Particularly, Chimasorb 944 manufactured by Allied Chemical Corporation of Morristown, N.J., is added in the amount of 0.75% by weight of the spun-bonded layers during the forming of the spun-bonded layers.

Sample 23 is an SMS fabric laminate made in accordance with the present invention. The internal melt-blown layer of Sample 23 is formed of isotactic polypropylene and having a basis weight of 0.60 oz/yd². The external spun-bonded layers were formed from a blend of isotatic polypropylene and 5% by weight of polybutylene. Each spun-bonded layer has a basis weight of 0.60 oz/yd² for a total basis weight of 1.8 oz/yd².

A comparison of the particle emission for Samples 17 through 23 is set forth in Table 6 below.

As can be seen from Table 6, the samples made in accordance with the present invention, Samples 19 through 22, produce far less particle emissions than the conventional SMS fabric laminates, Samples 17 and 18. The particle count for particles less than 0.5 microns was ten times less for Samples 19 through 22 than for the conventional polypropylene Samples 17 and 18. Even Sample 23, with its blend of polypropylene and 5% polybutylene used for making its spun-bonded layers, outperformed the conventional polypropylene Samples 17 and 18.

In order to further demonstrate the low emission characteristics of the SMS fabric laminate made from a low crystalline olefin copolymer, clean room garments were fabricated and used in the operation of a class 10 clean room laundry. A class 10 clean room laundry launders and packages clean room garments. The clean room garment embodying the present invention is shown in FIG. 7. The garment shown in FIG. 7 is in most respects the same as the protective garments sold by Kimberly-Clark under the trademark Kleen-Guard ®. The garment shown in FIG. 7 is different in several ways. The garment is made from the SMS fabric laminate of the present invention. In addition the test garments were fabricated with monofilament nylon thread and the fabric was double rolled around the elastic at the cuffs of the arms and legs to minimize particulate emission from the elastic.

The particular clean room laundry used to test the garments made in accordance with the present invention was in the business of laundering and packaging conventional woven polyester garments and conventional garments made of Tyvek ®. Tyvek ® is a registered trademark of Dupont of Wilmington, Del. For the purpose of the test, a Climet CI-8060 particle counter was set up inside the clean room laundry, and samples were taken at various locations. The workers, 3–4 per shift, were monitored for particulate emissions while wearing the following garments:

Garment 1. Woven polyester, manufactured by Mars White Knight or HiTech;

Garment 2. 1.75 oz/yd² SMS fabric laminate (C/P/C; 3.2% ethylene) unsterile; and Garment 3. 1.75 oz/yd² SMS fabric laminate (C/P/C; 3.2% ethylene) sterile (gamma).

TABLE 6

| | 17 Conventional (Sample 13 Table 5) | 18 Conventional (Sample 14 Table 5) | 19 Low Emission 3.2% PE (Sample 16 Table 5) | 20 Low Emission 3.2% PE (Sample 15 Table 5) | 21 Low Emission 3.2% PE | 22 Low Emission 3.2% PE Sterile | 23 Low Emission Blend |
|---|---|---|---|---|---|---|---|
| Material | P/P/P | P/P/P | C P C | C P C | C P C | C P C | C P C |
| Total Basis Weight (oz/yd²) | 1.80 | 1.50 | 1.75 | 1.80 | 1.75 | 1.75 | 1.80 |
| Melt-blown (oz/yd²) | 0.60 | 0.45 | 0.42 | 0.60 | 0.42 | 0.42 | 0.60 |
| Bond Pattern | EHP | HP | 714 | EHP | 714 | 714 | EHP |
| Area (ft²) | 4.50 | 9.62 | 9.62 | 4.50 | 9.62 | 9.62 | 2.67 |
| Particles >5.0 μ | 18.05 | | 1.55 | 0.25 | | | 6.20 |
| Particles >1.0 μ | 76.52 | | 5.17 | 1.83 | | | 36.89 |
| Particles >0.5 μ | 181.96 | 98.12 | 8.99 | 3.03 | 5.60 | 3.56 | 65.00 |
| Particles >0.3 μ | 247.61 | | 12.39 | 4.95 | | | 86.01 |

Garment 1 of woven polyester is a conventional clean room garment. Garments 2 and 3 are garments fabricated in accordance with the present invention from an SMS fabric laminate having the external spun-bonded layers formed from a low crystalline propylene copolymer of 3.2% ethylene and the internal melt-blown layer formed from isotatic polypropylene. Sterilization was done by gamma rays in conventional fashion. All workers wore woven polyester hoods (Mars White Knight or HiTech), woven polyester boots (HiTech), and vinyl gloves at all times.

It should be noted that the work conducted inside the clean room laundry, laundering, fluffing, folding, and packaging, can cause considerable amount of variability in the amount of generated particulate. Because of this, the matrix for conducting the test included testing with respect to each of the jobs performed in the clean room laundry and during the laundering of the different conventional garments, Tyvek® and woven polyester garments. The matrix of garments worn and garments laundered is set forth in Table 7, below:

TABLE 7

| GARMENTS LAUNDERED | GARMENTS WORN | | |
|---|---|---|---|
| | Garment 1 Woven Polyester | Garment 2 SMS (3.2% E) Unsterile | Garment 3 SMS (3.2% E) Sterile |
| Woven Polyester | 1/1 | | 3/1 |
| Tyvek Coveralls | 1/2 | 2/2 | 3/2 |
| Tyvek Hood/Boots | 1/3 | | 3/3 |

The blanks in Table 7 resulted from the inability to complete all segments of the matrix because of the commercial laundry's production schedule.

In taking the particle emission data, sampling was done at the various locations about the clean room. It was determined that the area of greatest particle emissions was under the feet of the worker whose job was fluffing and folding the laundered garments. This particular job was continuously performed whereas other jobs in other areas were only performed sporadically and on a limited basis. Therefore, all of the measurements were made at the location where the fluffing and folding was performed. Moreover, the worker at the location of the fluffing and folding during the 2½ days of testing was the same person, thereby eliminating variation resulting from different individuals.

Data were taken and statistically analyzed according to Federal Standard 209D. It should be noted that this standard requires the use of a number of locations to determine the classification of a clean room. For the purpose of this study, analysis of the garments worn only in the one location (fluffing and folding) was used in order to assure worst case performance. It was believed that the other locations, because of the limited use, would give misleadingly positive results as to the performance of all of the garments.

In order to comply with Federal Standard 209D particulate levels were measured at one particle size (usually 0.5 microns) and statistically analyzed. The upper confidence limit at 95% was then compared to the classifications for the clean room set forth in Table 4, above. The results of the testing is shown in FIG. 6. The matrix entries 1/2, 1/3, and 1/1 represent data taken while the conventional woven polyester garment was being worn and therefore those entries and the corresponding data are the control entries. When the two inventive garments, garments 2 and 3, were substituted for the conventional woven polyester garment, the particulate count descreased in all cases where the materials of the garments being laundered remained the same. Consequently, one can conclude that the garments made in accordance with the present invention themselves produced less particulate emission than conventional woven polyester clean room garments.

We claim:

1. A nonwoven fabric laminate consisting essentially of a first layer of spunbonded thermoplastic filaments formed from a first thermoplastic polymer and a second layer of discrete meltblown thermoplastic fibers formed from a second thermoplastic polymer, wherein the layers are positioned in laminar surface-to-surface relationship, wherein the layers are heat bonded in discrete areas, and wherein the thermoplastic polymer in at least said first layer is an olefin copolymer having a crystallinity of less than 45%.

2. The nonwoven fabric laminate of claim 1, wherein the olefin copolymer has a crystallinity between 31–35%.

3. The nonwoven fabric laminate of claim 2, wherein the olefin copolymer has a crystallinity of about 32%.

4. The nonwoven fabric laminate of claim 1, wherein the olefin copolymer is polypropylene modified by copolymerizing 0.5–5.0% ethylene randomly in the backbone.

5. The nonwoven fabric laminate of claim 4, wherein the olefin copolymer has a crystallinity between 31–35%.

6. The nonwoven fabric laminate of claim 5, wherein the olefin copolymer has a crystallinity of about 32%.

7. A nonwoven fabric laminate consisting essentially of a first layer of spunbonded thermoplastic filaments formed from a first thermoplastic polymer and a second layer of discrete meltblown thermoplastic fibers formed from a second thermoplastic polymer, wherein the layers are positioned in laminar surface-to-surface relationship, wherein the layers are heat bonded in discrete areas, and wherein the thermoplastic polymer in at least said first layer is an olefin terpolymer having a crystallinity of less than 45%.

8. The nonwoven fabric laminate of claim 7, wherein the olefin terpolymer has a crystallinity between 31–35%.

9. The nonwoven fabric laminate of claim 8, wherein the olefin terpolymer has a crystallinity of about 32%.

10. A nonwoven fabric laminate consisting essentially of in sequence a first layer of spunbonded thermoplastic filaments formed from a first thermoplastic polymer, a second layer of meltblown thermoplastic fibers formed from a second thermoplastic polymer, and a third layer of spunbonded thermoplastic filaments formed from a thermoplastic polymer, wherein the layers are heat bonded in discrete areas and wherein each of the first and third layer thermoplastic polymers is an olefin copolymer having a crystallinity of less than 45%.

11. The nonwoven fabric laminate of claim 10, wherein the olefin copolymer has a crystallinity between 31–35%.

12. The nonwoven fabric laminate of claim 11, wherein the olefin copolymer has a crystallinity of about 32%.

13. The nonwoven fabric laminate of claim 10, wherein the olefin copolymer is polypropylene modified by copolymerizing 0.5–5.0% ethylene randomly in the backbone.

14. The nonwoven fabric laminate of claim 13, wherein the olefin copolymer has a crystallinity between 31–35%.

15. The nonwoven fabric laminate of claim 14, wherein the olefin copolymer has a crystallinity of about 32%.

16. A nonwoven fabric laminate consisting essentially of in sequence a first layer of spunbonded thermoplastic filaments formed from a first thermoplastic polymer, a second layer of meltblown thermoplastic fibers formed from a second thermoplastic polymer, and a third layer of spunbonded thermoplastic filaments formed from a third thermoplastic polymer, wherein the layers are heat bonded in discrete areas and wherein each of the first and third layer thermoplastic polymers is an olefin terpolymer having a crystallinity of less than 45%.

17. The nonwoven fabric laminate of claim 16, wherein the olefin terpolymer has a crystallinity between 31–35%.

18. The nonwoven fabric laminate of claim 17, wherein the olefin terpolymer has a crystallinity of about 32%.

19. A low particle emitting garment constructed from a nonwoven fabric laminate consisting essentially of in sequence a first layer of spunbonded thermoplastic filaments formed from a first thermoplastic polymer, a second layer of meltblown thermoplastic fibers formed from a second thermoplastic polymer, and a third layer of spunbonded thermoplastic filaments formed from a third thermoplastic polymer, wherein the layers are heat bonded in discrete areas and wherein each of the first and third layer thermoplastic polymers is an olefin copolymer having a crystallinity of less than 45%.

20. The garment of claim 19, wherein the olefin copolymer has a crystallinity between 31–35%.

21. The garment of claim 20, wherein the olefin copolymer has a crystallinity of about 32%.

22. The garment of claim 21, wherein the olefin copolymer is polypropylene modified by copolymerizing 0.5–5.0% ethylene randomly in the backbone.

23. The garment of claim 22, wherein the garment emits less than 10 particles, less than 0.5 micron in size, per square foot of fabric laminate per cubic foot per minute of air.

24. A medical sterile wrap constructed from a nonwoven fabric laminate consisting essentially of a first layer of spunbonded thermoplastic filaments formed from a first thermoplastic polymer and a second layer of discrete meltblown thermoplastic fibers formed from a second thermoplastic polymer, wherein the layers are positioned in laminar surface-to-surface relationship, wherein the layers are heat bonded in discrete areas, and wherein the thermoplastic polymer in at least said first layer is an olefin copolymer having a crystallinity of less than 45%.

25. The medical sterile wrap of claim 24, wherein the olefin copolymer has a crystallinity between 31–35%.

26. The medical sterile wrap of claim 25, wherein the olefin copolymer has a crystallinity of about 32%.

27. The medical sterile wrap of claim 24, wherein the olefin copolymer is polypropylene modified by copolymerizing 0.5–5.0% ethylene randomly in the backbone.

28. The medical sterile wrap of claim 27, wherein the olefin copolymer has a crystallinity between 31–35%.

29. The medical sterile wrap of claim 28, wherein the olefin copolymer has a crystallinity of about 32%.

30. A medical sterile wrap constructed from a nonwoven fabric laminate consisting essentially of a first layer of spunbonded thermoplastic filaments formed from a first thermoplastic polymer and a second layer of discrete meltblown thermoplastic fibers formed from a second thermoplastic polymer, wherein the layers are positioned in laminar surface-to-surface relationship, wherein the layers are heat bonded in discrete areas, and wherein the thermoplastic polymer in at least first layer is an olefin terpolymer having a crystallinity of less than 45%.

31. The medical sterile wrap of claim 30, wherein the olefin terpolymer has a crystallinity between 31–35%.

32. The medical sterile wrap of claim 31, wherein the olefin terpolymer has a crystallinity of about 32%.

33. A medical sterile wrap constructed from a nonwoven fabric laminate consisting essentially of in sequence a first layer of spunbonded thermoplastic filaments formed from a first thermoplastic polymer, a second layer of meltblown thermoplastic fibers formed from a second thermoplastic polymer, and a third layer of spunbonded thermoplastic filaments formed from a third thermoplastic polymer, wherein the layers are heat bonded in discrete areas and wherein each of the first and third layer thermoplastic polymers is an olefin copolymer having a crystallinity of less than 45%.

34. The medical sterile wrap of claim 33, wherein the olefin copolymer has a crystallinity between 31–35%.

35. The medical sterile wrap of claim 34, wherein the olefin copolymer has a crystallinity of about 32%.

36. The medical sterile wrap of claim 35, wherein the olefin copolymer is polypropylene modified by copolymerizing 0.5–5.0% ethylene randomly in the backbone.

37. The medical sterile wrap of claim 36, wherein the olefin copolymer has a crystallinity between 31–35%.

38. The medical sterile wrap of claim 37, wherein the olefin copolymer has a crystallinity of about 32%.

39. A medical sterile wrap constructed from a nonwoven fabric laminate consisting essentially of in sequence a first layer of spunbonded thermoplastic filaments formed from a first thermoplastic polymer, a second layer of meltblown thermoplastic fibers formed from a second thermoplastic polymer, and a third layer of spunbonded thermoplastic filaments formed from a third thermoplastic polymer, wherein the layers are heat bonded in discrete areas and wherein each of the first and third layer thermoplastic polymers is an olefin terpolymer having a crystallinity of less than 45%.

40. The medical sterile wrap of claim 39, wherein the olefin terpolymer has a crystallinity between 31–35%.

41. The medical sterile wrap of claim 40, wherein the olefin terpolymer has a crystallinity of about 32%.

42. A surgical gown constructed from a nonwoven fabric laminate consisting essentially of a first layer of spunbonded thermoplastic filaments formed from a first thermoplastic polymer and a second layer of discrete meltblown thermoplastic fibers formed from a second thermoplastic polymer, wherein the layers are positioned in laminar surface-to-surface relationship, wherein the layers are heat bonded in discrete areas, and wherein the thermoplastic polymer in at least said first layer is an olefin copolymer having a crystallinity of less than 45%.

43. The surgical gown of claim 42, wherein the olefin copolymer has a crystallinity between 31–35%.

44. The surgical gown of claim 43, wherein the olefin copolymer has a crystallinity of about 32%.

45. The surgical gown of claim 42, wherein the olefin copolymer is polypropylene modified by copolymerizing 0.5-5.0% ethylene randomly in the backbone.

46. The surgical gown of claim 45, wherein the olefin copolymer has a crystallinity between 31-35%.

47. The surgical gown of claim 46, wherein the olefin copolymer has a crystallinity of about 32%.

48. A surgical gown constructed from a nonwoven fabric laminate consisting essentially of a first layer of spunbonded thermoplastic filaments formed from a first thermoplastic polymer and a second layer of discrete meltblown thermoplastic fibers formed from a second thermoplastic polymer, wherein the layers are positioned in laminar surface-to-surface relationship, wherein the layers are heat bonded in discrete areas, and wherein the thermoplastic polymer in at least said first layer is an olefin terpolymer having a crystallinity of less than 45%.

49. The surgical gown of claim 48, wherein the olefin terpolymer has a crystallinity between 31-35%.

50. The surgical gown of claim 49, wherein the olefin terpolymer has a crystallinity of about 32%.

51. A surgical gown constructed from a nonwoven fabric laminate consisting essentially of in sequence a first layer of spunbonded thermoplastic filaments formed from a first thermoplastic polymer, a second layer of meltblown thermoplastic fibers formed from a second thermoplastic polymer, and a third layer of spunbonded thermoplastic filaments formed from a third thermoplastic polymer, wherein the layers are heat bonded in discrete areas and wherein each of the first and third layer thermoplastic polymers is an olefin copolymer having a crystallinity of less than 45%.

52. The surgical gown of claim 51, wherein the olefin copolymer has a crystallinity between 31-35%.

53. The surgical gown of claim 52, wherein the olefin copolymer has a crystallinity of about 32%.

54. The surgical gown of claim 51, wherein the olefin copolymer is polypropylene modified by copolymerizing 0.5-5.0% ethylene randomly in the backbone.

55. The surgical gown of claim 54, wherein the olefin copolymer has a crystallinity between 31-35%.

56. The surgical gown of claim 55, wherein the olefin copolymer has a crystallinity of about 32%.

57. A surgical gown constructed from a nonwoven fabric laminate consisting essentially of in sequence a first layer of spunbonded thermoplastic filaments formed from a first thermoplastic polymer, a second layer of meltblown thermoplastic fibers formed from a second thermoplastic polymer, and a third layer of spunbonded thermoplastic filaments formed from a third thermoplastic polymer, wherein the layers are heat bonded in discrete areas and wherein each of the first and third layer thermoplastic polymers is an olefin terpolymer having a crystallinity of less than 45%.

58. The surgical gown of claim 57, wherein the olefin terpolymer has a crystallinity between 31-35%.

59. The surgical gown of claim 58, wherein the olefin terpolymer has a crystallinity of about 32%.

60. A sterilizable clean room garment constructed from a nonwoven fabric laminate consisting essentially of in sequence a first layer of spunbonded thermoplastic filaments formed from a first thermoplastic polymer, a second layer of meltblown thermoplastic fibers formed from a second thermoplastic polymer, and a third layer of spunbonded thermoplastic filaments formed from a third thermoplastic polymer, wherein the layers are heat bonded in discrete areas and wherein each of the first and third layer thermoplastic polymers is an olefin copolymer having a crystallinity of less than 45%.

61. The sterilizable clean room garment of claim 60, wherein the olefin copolymer has a crystallinity between 31-35%.

62. The sterilizable clean room garment of claim 61, wherein the olefin copolymer has a crystallinity of about 32%.

63. The sterilizable clean room garment of claim 60, wherein the olefin copolymer is polypropylene modified by copolymerizing 0.5-5.0% ethylene randomly in the backbone.

64. The garment of claim 63, wherein the garment emits less than 10 particles, less than 0.5 micron in size, per square foot of fabric laminate per cubic foot per minute of air.

* * * * *

UNITED STATES PATENT AND TRADEMARK OFFICE
CERTIFICATE OF CORRECTION

PATENT NO. : 5,188,885

DATED : February 23, 1993

INVENTOR(S) : T. K. Timmons, S. R. Stopper, N. K. Fox, D. S. Everhart, W. Conn and L. A. Morell It is certified that error appears in the above-identified patent and that said Letters Patent is hereby corrected as shown below:

Column 4, line 53, "Boom, and C. D. Fluharty" should read --..Boon, and C. D. Fluharty...--.

Column 7, line 58, "("P P P")" should read --("P/P/P")--;

Column 10, Table 2, please move sample results to last line of table (MD/CD 6.68...);

Table 2, please move sample results to last line of table (Face/Anvil 20/72...); Should read -- 20/12--.

Table 2, please move sample results to last line of table (MD/CD 3.89/2.1). Should read --3.8/2.1 --.

Column 12, Table 3, please move sample results to last line of table (in/lbs) MD/CD 3 wks).

Columns 15-16, Table 6, all material components should have slashes: C/P/C.

Signed and Sealed this

Eleventh Day of October, 1994

Attest:

BRUCE LEHMAN

*Attesting Officer*     *Commissioner of Patents and Trademarks*